(12) United States Patent
Seelig et al.

(10) Patent No.: US 8,821,790 B2
(45) Date of Patent: Sep. 2, 2014

(54) DIAGNOSTIC MEASURING SYSTEM

(71) Applicant: Roche Diagnostics Operations, Inc., Indianapolis, IN (US)

(72) Inventors: Peter Seelig, Frankfurt am Main (DE); Helmut Leininger, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/863,779

(22) Filed: Apr. 16, 2013

(65) Prior Publication Data

US 2013/0230428 A1    Sep. 5, 2013

Related U.S. Application Data

(60) Division of application No. 12/940,368, filed on Nov. 5, 2010, now Pat. No. 8,449,823, which is a continuation of application No. PCT/EP2009/055450, filed on May 6, 2009.

(30) Foreign Application Priority Data

May 6, 2008   (EP) .................................. 08155742

(51) Int. Cl.
```
G01N 31/00      (2006.01)
A61B 5/145      (2006.01)
G01N 33/487     (2006.01)
G01N 21/55      (2014.01)
A61B 5/1455     (2006.01)
B01L 3/00       (2006.01)
B01L 9/00       (2006.01)
G01N 21/84      (2006.01)
G01N 33/66      (2006.01)
```

(52) U.S. Cl.
CPC ............ *G01N 21/55* (2013.01); *A61B 5/14532* (2013.01); *G01N 33/48764* (2013.01); *A61B 2562/0295* (2013.01); *A61B 5/1455* (2013.01); *B01L 3/505* (2013.01); *B01L 2300/0841* (2013.01); *B01L 9/523* (2013.01); *B01L 2300/0654* (2013.01); *B01L 2300/0825* (2013.01); *G01N 21/8483* (2013.01); *G01N 33/66* (2013.01); *B01L 2300/0812* (2013.01)
USPC ............ 422/66; 422/400; 422/63; 422/82.05

(58) Field of Classification Search
USPC ................................. 422/66, 400, 63, 82.05
See application file for complete search history.

(56) References Cited

U.S. PATENT DOCUMENTS

| 7,262,061 B2 | 8/2007 | Petrich et al. |
| 2005/0232815 A1 | 10/2005 | Ruhl et al. |
| 2006/0002816 A1 | 1/2006 | Zimmer et al. |

FOREIGN PATENT DOCUMENTS

| EP | 1593434 | 11/2005 |
| WO | WO 01/48461 | 7/2001 |
| WO | WO 2004/056269 | 7/2004 |

*Primary Examiner* — Sam P Siefke
(74) *Attorney, Agent, or Firm* — Roche Diagnostics Operations, Inc.

(57) ABSTRACT

The invention concerns a diagnostic tape unit with a test tape that can be wound onto a spool which comprises a transport tape and a plurality of test elements mounted thereon, where the test elements have an analytical reagent layer, a carrier foil supporting the reagent layer and a piece of adhesive tape connecting the carrier foil with the transport tape, and where the front side of the reagent layer facing away from the carrier foil is designed for the application of a sample substance. According to the invention it is proposed that the test elements in combination with the light transmitting transport tape in each case form an optical multi-layer system for a rear-side reflection-photometric measurement of the reagent layer.

20 Claims, 2 Drawing Sheets

US 8,821,790 B2

DIAGNOSTIC MEASURING SYSTEM

CLAIM OF PRIORITY

The present application is a divisional of U.S. patent application Ser. No. 12/940,368 filed on Nov. 5, 2010, which is a continuation application based on and claiming priority to international application PCT/EP2009/055450, filed May 6, 2009, which claims the priority benefit of European Application 08155742.3, filed May 6, 2008, each of which are hereby incorporated by reference in their respective entireties.

TECHNICAL FIELD OF THE INVENTION

The invention concerns a diagnostic tape unit, in particular a tape cassette for blood sugar tests with a test tape that is wound onto or can be wound onto a spool as a tape reel, the test tape comprising a transport tape and a plurality of test elements which are mounted thereon. The invention additionally concerns a measuring system for the use of such a tape unit.

BACKGROUND

Tape units have been designed for blood sugar tests in order to further improve the user-friendliness compared to test strip systems available on the market. Thus, in order to simplify the handling, a large number of test elements can be compactly stored on a rollable transport tape and also be disposed of again after use by means of the tape transport. Such a tape unit can be advantageously inserted into a hand-held device as a consumable in the form of a cassette in order to allow the user to carry out substantially automated self tests.

With conventional dry chemistry test strips, reagent fields are mounted on a relatively thick reagent carrier. An optical reflection measurement can be carried out relatively easily with such a one-layer system. However, a test tape with a plurality of tests that is spooled in the form of a tape reel cannot be realized with this.

On this basis the object of the invention is to further develop the tape concepts known in the prior art and to specify a tape unit designed for a reliable measurement even as a mass-produced article of the type stated above as well as a measuring system therefor.

SUMMARY

This object and others that will be appreciated by a person of ordinary skill in the art have been achieved according to the embodiments of the present invention disclosed herein. In one embodiment, the present invention comprises a diagnostic tape unit, in particular a tape cassette for blood sugar tests with a test tape that is wound onto or can be wound onto a spool as a tape reel, the test tape comprising a transport tape and a plurality of test elements which are mounted thereon, where the test elements include an analytical reagent layer, a carrier foil supporting the reagent layer and a piece of adhesive tape connecting the carrier foil with the transport tape, and where the front side of the reagent layer facing away from the carrier foil is designed for the application of a sample substance.

The combination of features stated in the independent patent claims is proposed to achieve this object. Advantageous embodiments and further developments of the invention are derived from the dependent claims.

The embodiments of the present invention are based on the idea of enabling a sample application on the front-side and measurement on the rear side with a test tape having spaced apart test fields. Accordingly it is proposed according to the embodiments that the test elements in combination with the light transmitting transport tape in each case form an optical multi-layer system for a rear-side, reflection-photometric measurement of the reagent layer. The multi-layer assembly enables relatively thin prefabricated test carriers to be integrated into a tape reel and the uniform optical multi-layer composite enables the reflectance to be detected by a measuring apparatus at an exposed section of the test tape independently of the handling side.

In order to obtain a measuring signal which has the required quality for diagnostic applications, when the refractive index and/or the transmission and/or the haze of the layers of the multi-layer system is formed by the carrier foil, the piece of adhesive tape and the transport tape are matched on each other within predetermined tolerances. In this connection it is particularly advantageous when the refractive index of the transport tape, the carrier tape and the piece of adhesive tape is in each case between about 1.4 and 1.7, for example between about 1.5 and 1.6.

Interfering effects can be further reduced by means of the fact that the individual layers of the multi-layer system have a maximum refractive index difference of about 0.2, for example less than about 0.1.

In one embodiment, the total refractive index is about 1.5, and the deviation in the refractive index is less than 0.1.

Further improvements can be achieved when the transport tape, the piece of adhesive tape and the carrier foil each have a transmission in the visible wavelength range of more than about 80%, for example between about 85% and 92%, and when the total transmission of the multi-layer system in the visible wavelength range is at least about 80%.

For a reproducible measurement, in certain embodiments the transmission tolerance is less than 5% for the entirety of the test elements of a test tape.

In order to adequately reduce scattering losses it is advantageous when the optical haze of the carrier tape and of the piece of adhesive tape in the visible wavelength range is less than 10%, for example about 8%. It is also favorable when the optical haze of the transport tape in the visible wavelength range is less than 3%, for example about 2.5%, and when the total optical haze of the multi-layer system in the visible wavelength range is less than 20%, for example about 15%.

In order to be able to take into consideration interfering effects due to the manufacturing process, a decrease in the haze of the multi-layer system should take place in a given time interval in particular of about 1 to 2 weeks after its manufacture, where subsequently the haze should remain relatively constant.

In order to adequately limit variants within a given tape unit, the haze tolerance for the entirety of the multi-layer systems of a test tape should be less than about 5%.

In other embodiments, a multi-layer piece of adhesive tape is used which comprises a transparent foil substrate furnished on both sides with an adhesive layer.

In yet other embodiments, the transport tape and the carrier foil comprise a PET film. In general polymer foils can be used. In addition to polyethylene terephthalate (PET), other examples of materials for the transport tape and carrier foil are polyvinyl fluoride (PVF), polyethylene (PE), polypropylene (PP), polyvinylidene difluoride (PVDF), polyvinyl chloride (PVC), polystyrene (PS), ethylene/tetrafluoroethylene copolymers (ETFE), polycarbonate and propylene carbonate.

In yet other embodiments, the thickness of the carrier foil is between about 20 and 25 μm, the thickness of the transport tape is between about 10 and 15 μm and the thickness of the piece of adhesive tape is between about 30 and 50 μm.

In order to take into account interfering effects which result from a specific configuration, in embodiments in which an analyte contained in the sample substance in particular in the form of a body fluid, in particular blood, is determined by a relative reflectance measurement, calibration data are typically assigned to the test elements which define the concentration of the analyte as a function of the measured reflectance.

Another aspect of the invention concerns a diagnostic measuring system in particular for blood sugar tests with a diagnostic tape unit according to the invention and a reflection photometric arrangement oriented towards the rear side of the reagent layer of the test element located in a measuring position which comprises a light source and a photodetector where the detector is arranged outside the direct reflection path of the measuring light radiated by the light source through the multi-layer system onto the reagent layer.

In this connection in certain embodiments the light source generates a light spot of less than about 1 $mm^2$ on the rear side of the reagent layer where a granularity of the reagent layer serves as a diffuser.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
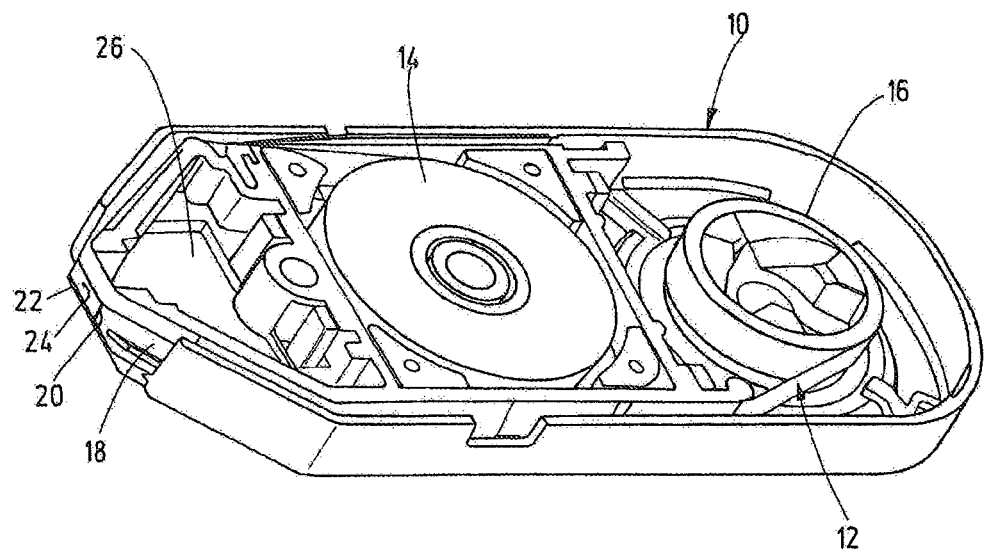
FIG. 1 shows a diagnostics tape unit in the form of a tape cassette in a sectional perspective view.

The tape cassette 10 shown in FIG. 1 can be used as a consumable in a hand-held device (not shown) to carry out a plurality of blood sugar self-tests. The cassette comprises a test tape 12, a supply spool 14 to unwind unused test tape and a take-up spool 16 to wind used test tape, where the test tape 12 has a rollable transport tape 18 and a plurality of spaced-apart test elements 20 mounted thereon.

The unused test tape is stored protected from environmental influences in the form of a tape reel on the supply spool 14. The test tape 12 can be wound on by means of a rotary drive which engages with the take-up spool 16 such that the test elements 20 can be successively made available for the user at an application site 22. At this site a drop of blood can be applied in a simple manner on the exposed front side 24 of the respective active test element 20, while a rear-side reflection-photometric measurement is carried out by a measuring arrangement in the instrument that engages in the measuring chamber 26 of the cassette 10. The used section of test tape is disposed of on the take-up spool 16. In this manner it is possible to process approximately 50 tests without requiring instrument intervention or laborious operating steps by the user.

Figure 2:
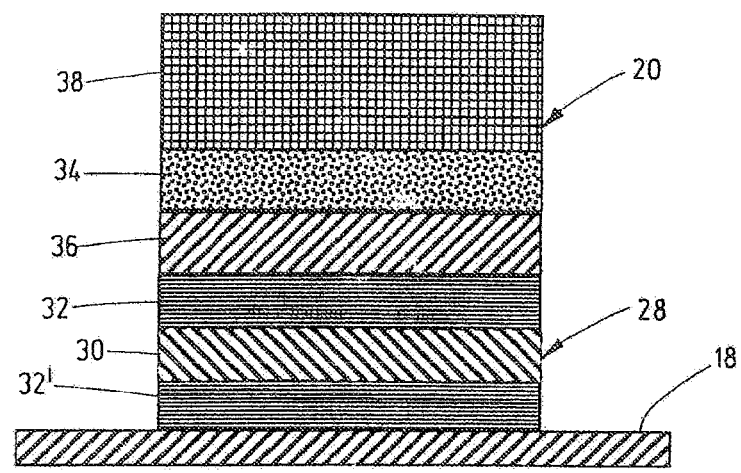
FIG. 2 shows the test tape of the tape cassette in a longitudinal section of a part thereof in the area of a test element.

As shown in FIG. 2, the transport tape 18 together with the attached test elements 20 forms a multi-layer composite structure or a multi-layer system which is based on a simple manufacturing process as described in EP-A 1 593 434, the disclosure of which is hereby incorporated by reference herein in its entirety. The test elements 20 are glued onto the transport tape 18 as test labels by means of a piece of double-sided adhesive tape 28. For this purpose the piece of adhesive tape 28 comprises a liner foil 30 which is furnished on both sides with an adhesive layer 32, 32'. The detection reaction takes place in a thin reagent layer 34 which is applied to a carrier foil 36 as a dry substance and which is held there by means of a piece of adhesive tape 28. The magnitude of a color change of the reagent is in this connection functionally related to the concentration of the analyte to be measured (in this case blood glucose). The applied body fluid can be spread two-dimensionally on the application side of the reagent layer 34 by means of a net-like spreading layer 38.

The glucose concentration is determined by reflectance photometry in which a relative reflectance value is determined as a quotient of the end value and the start value of the test element 20 in order to take into account constant interfering factors. For this the initial reflectance value of the test element is measured before sample application and the reflectance is measured again after a time interval after adding the sample to the reagent layer. The first measurement as well as the subsequent measurements include interfering factors which irrespective of the wanted signal make contributions to the measured signal. The sample concentration is then calculated by means of a calculation rule (function curve) stored in the instrument. This function curve can be determined by calibrating the measuring system. Hence, this allows constant interfering factors to be taken into consideration for the system calibration.

However, for a reliable reflectance measurement the optical interfering effects must be small compared to the measured signal. In the case of conventional test strips, measurements are made only through a one-layer reagent carrier, whereas different foils and adhesive layers must be taken into account in the multi-layer composite structure according to FIG. 1. In this connection it should be noted that all foils available on the market have tolerances with regard to their optical specifications which are due to the manufacturing processes. Thus, the optical light path is affected by the transparency, absorption, refractive index and scattering parameters of each individual component and by the interaction of the components that are used.

Hence, in order to be able to carry out a reflectance measurement with the accuracy required for blood sugar measurements, it is not possible to use just any foils, but rather in the multi-layer tape configuration described above special precautionary measures and matching with regard to the optical properties are necessary as summarized in the following in table 1.

The magnitude of the wanted signal decreases with increasing transparency or transmission of the foils. In addition the signal quality is also affected by the surface scattering and volume scattering. Both together can be detected by a measurement of opacity. The said parameters can be determined by a standard measurement procedure according to the ASTM-D 1003-61 method A standard (standard test method for haze and luminous transmittance of transparent plastics). In this procedure the scattering in the forwards direction of the transmitted light is detected by means of a so-called haze meter such as that which is for example sold under the trade name "BYK Gardner Haze-Gard Plus". The mode of operation of this instrument is based on irradiating a collimated bundle of light centrally through a foil sample into the entrance of an Ulbricht sphere in which a light trap is disposed at a sphere exit that is diametrically opposite to the sphere entrance and the scattered light is detected at an angle of 90° centrally in relation to the axis of the through beam. This allows a differentiation to be made between unscattered light and light scattered by the haze of the foil in the forwards direction. An area of the sphere is covered by a scattering standard for the transmission measurement.

Surprisingly it turned out that such haze measurements in the forwards direction also enable an influencing variable to also be obtained for reflectance measurements in the backwards direction where the influencing variable can be measured using standardized instruments. It was found that for a multi-layer structure there was a linear relationship between the reflectance blank value detected in the diagnostic measuring system and the material parameter detected in the haze meter (haze H) as a function of the layer thickness. In this manner it is possible to translate a variation in the scattering which is still acceptable for the actual measurement signal into a defined tolerance range of the haze signal and thus ensure a quality control for the foils that are used. In this connection it must be born in mind that as the haze increases the ranges for variation and tolerance must also be restricted.

In one embodiment, the long flexible transport tape 18 comprises PET and has a thickness d of about 12 μm and a refractive index n of about 1.6. In such an embodiment, the transport tape 18 should be substantially light permeable or transparent and the spectral transmission T in the wavelength range between about 400 and 900 nm should be more than about 85%. The haze (haze H) should be at about 2.5%. As stated above the adherence of tolerance ranges (tolerance widths) ensures measuring precision within the allowed limits in a mass production. The transmission tolerance $\Delta T$ should be less than 2% for the transport tape 18 cut to the required length, and the haze should vary by less than 0.5%.

The other layers in the multi-layer system should be specially matched according to table 1:

TABLE 1

|  | d | n | T | $\Delta T$ | H | $\Delta H$ |
| --- | --- | --- | --- | --- | --- | --- |
| transport tape 18 | 12 μm | 1.6 | >88% | <2% | 2.5% | <0.5% |
| piece of adhesive tape 28 | 42 μm | 1.5 | >85% | <3% | 8.0% | <3% |
| PET carrier foil 36 | 23 μm | 1.6 | >88% | <2% | 8.0% | <1% |
| total system 18, 28, 36 | 77 μm | 1.5 | >80% | <5% | 15% | <5% |

The uniformly determined measured values for the total assembly comprising transport tape 18, piece of adhesive tape 28 and carrier foil 36 are stated in the last line of table 1. A particular problem was observed for the total system with regard to the stability of the measured values in that there was a decrease in the haze values within the first one to two weeks after manufacture. Afterwards the measured values remained essentially stable over time. The individual components do not exhibit such a behavior before their assembly. An explanation is that the initially increased haze is due to the inclusion of air bubbles when the individual components are assembled to form the total system which results in an increased scattering. The decrease in the measured haze values over time is then caused by the escape of the enclosed air by diffusion.

Figure 3:
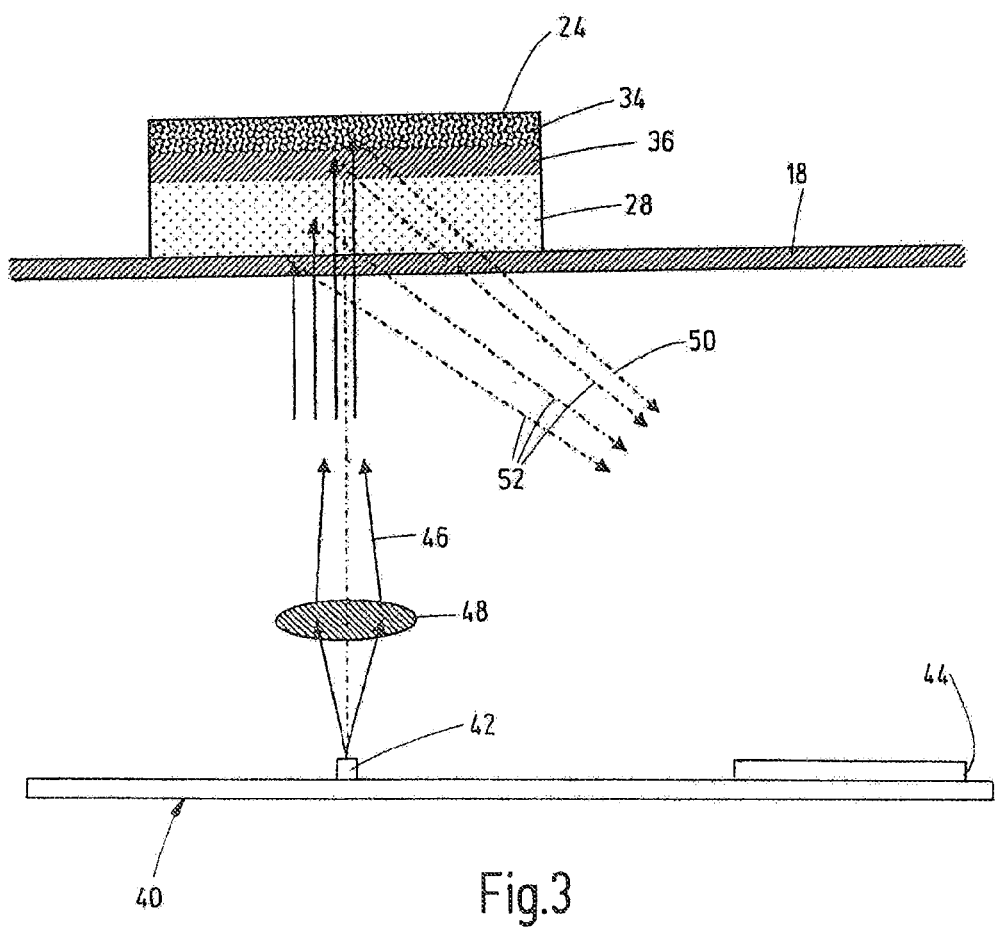
FIG. 3 shows a reflectometric measuring arrangement oriented towards the test tape in a diagrammatic view.

FIG. 3 shows a diagnostic measuring system as implemented in a portable blood sugar measuring device with an inserted tape cassette 10. The measurement of the reagent layer 34 from the rear side is by means of a reflection photometric arrangement 40 in the instrument which comprises a light source (LED 42) and an optical detector (photodiode 44). The irradiated light beam 46 is focused by an optical system (collecting lens 48) onto a small light spot on the rear side of the reagent layer 44 where its granularity acts as scattering bodies. In this case the detector 44 is outside the range of angles of reflection of the directly reflected light fraction such that essentially only scattered light is detected.

Hence, the system is designed such that the test field formed by the reagent layer 34 is illuminated at high intensity. The measuring light thereby interacts with the reagent and is scattered as a function of absorption and transmission. The scattered useful light 50 impinges on the detector 44 according to the solid angle of detection. However, at the detector the interfering light 52 scattered or reflected by the other components 18, 28, 36 is also detected (the optical path is simplified symbolically in FIG. 3). The quality of the measurement signal is therefore derived from the ratio of useful light to interfering light. The described adaptation of the optical properties of the elements located in the optical path with regard to refractive index, transmission, absorption and scattering properties in the range of the illumination wavelength has the effect that the measurement signal corresponds to the required quality.

The functional relationship between the measured reflectance and the concentration of the analyte can be described by a calibration curve. The measuring instrument controlled by microelectronics can thus assign the correct concentration value to any determined reflectance and display this on a display. The calibration curve is determined using the same reagents in the described test field arrangement. The scattered light fractions resulting from the specific structure can therefore be taken into consideration in the calibration. The process-related variations of the different interfering factors occur within a certain tolerance. The allowed tolerance for these interfering factors is derived from the predetermined and allowed limits to the concentration level of the relevant analyte.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A diagnostic measuring system comprising:
a diagnostic tape unit comprising a tape cassette for blood sugar tests, the tape cassette having a test tape that is wound onto or can be wound onto a spool as a tape reel, the test tape comprising a light-transmitting transport tape and a plurality of spaced apart test elements mounted thereon, the test elements each comprising an analytical reagent layer supported on a carrier foil layer, and further including an adhesive tape layer connecting the carrier foil layer adhered on one side with the transport tape adhered on an opposite side, wherein a front side of the reagent layer faces away from the carrier foil layer and is configured for the application of a sample substance, the test elements in combination with the transport tape in each case foaming an optical multi-layer system for a rear-side reflection-photometric measurement of the reagent layer, wherein the transport tape, the adhesive tape layer and the carrier foil layer of each test element each have optical properties comprising refractive index, transmission and haze, and wherein at least one optical property of the transport tape, adhesive tape layer and carrier foil layer are matched within predetermined tolerances; and
a reflection photometric arrangement oriented towards the rear side of the reagent layer of the test element located in a measuring position, the reflection photometric arrangement comprising a light source and a photodetector where the photodetector is arranged outside the direct reflection path of the measuring light radiated by the light source through the multi-layer system onto the reagent layer.

2. The diagnostic measuring system according to claim 1, wherein the light source generates a light spot of less than about 1 mm$^2$ on the rear side of the reagent layer, wherein a granularity of the reagent layer serves as a scattering body.

3. The diagnostic measuring system according to claim 1, wherein the refractive index of the transport tape, the carrier tape and the adhesive tape is in each case between about 1.4 and 1.7.

4. The diagnostic measuring system according to claim 3, wherein the refractive index of the transport tape, the carrier tape and the adhesive tape is in each case between about 1.5 and 1.6.

5. The diagnostic measuring system according to claim 1, wherein the individual layers of the multi-layer system have a maximum refractive index difference of about 0.2.

6. The diagnostic measuring system according to claim 5, wherein the individual layers of the multi-layer system have a refractive index difference of less than about 0.1.

7. The diagnostic measuring system according to claim 1, wherein the total refractive index of the multi-layer system is about 1.5.

8. The diagnostic measuring system according to claim 1, wherein the transport tape, the adhesive tape and the carrier foil layer each have a transmission in the visible wavelength range of more than 80%.

9. The diagnostic measuring system according to claim 8, wherein the transport tape, the adhesive tape and the carrier foil layer each have a transmission in the visible wavelength range of between about 85% and 92%.

10. The diagnostic measuring system according to claim 1, wherein the total transmission of the multi-layer system in the visible wavelength range is at least about 80%.

11. The diagnostic measuring system according to claim 1, wherein the transmission tolerance is less than about 5% for the entirety of the test elements of a test tape.

12. The diagnostic measuring system according to claim 1, wherein the optical haze of the carrier foil layer and of the piece of adhesive tape in the visible wavelength range is less than about 10%.

13. The diagnostic measuring system according to claim 12, wherein the optical haze of the carrier foil layer and of the adhesive tape in the visible wavelength range is less than about 8%.

14. The diagnostic measuring system according to claim 1, wherein the optical haze of the transport tape in the visible wavelength range is less than about 3%.

15. The diagnostic measuring system according to claim 14, wherein the optical haze of the transport tape in the visible wavelength range is less than about 2.5%.

16. The diagnostic measuring system according to claim 1, wherein the total optical haze of the multi-layer system in the visible wavelength range is less than about 20%.

17. The diagnostic measuring system according to claim 16, wherein the total optical haze of the multi-layer system in the visible wavelength range is less than about 15%.

18. The diagnostic measuring system according to claim 1, wherein the adhesive tape comprises a transparent foil substrate furnished on both sides with an adhesive layer.

19. The diagnostic measuring system according to claim 1, wherein the transport tape and the carrier foil each comprise a PET film.

20. The diagnostic measuring system according to claim 1, wherein an analyte contained in a sample substance in the form of a body fluid can be determined by a relative reflectance measurement, wherein calibration data are assigned to the test elements which define the concentration of the analyte as a function of the measured reflectance.

* * * * *